United States Patent [19]

Wegner

[11] 4,226,939
[45] Oct. 7, 1980

[54] TREATMENT OF MAKE-UP WATER FOR USE IN A FERMENTATION PROCESS FOR GROWTH OF YEAST CELLS REQUIRING GROWTH FACTORS

[75] Inventor: Eugene H. Wegner, Bartlesville, Okla.

[73] Assignee: Phillips Petroleum Company, Bartlesville, Okla.

[21] Appl. No.: 875,667

[22] Filed: Feb. 6, 1978

[51] Int. Cl.$^3$ ............................................. C12N 1/32
[52] U.S. Cl. .................................. 435/247; 435/253; 435/255; 435/256; 435/804; 435/818; 435/822; 435/911
[58] Field of Search .................. 195/82, 114, 121, 96, 195/125, 108, 109, 110, 100; 210/62; 435/822, 911, 250, 255, 800, 804, 818, 930, 938, 247, 253, 256

[56] References Cited

U.S. PATENT DOCUMENTS

| | | | |
|---|---|---|---|
| 1,805,353 | 5/1931 | Berl | 210/62 X |
| 2,595,499 | 5/1952 | Wood et al. | 195/114 |
| 2,922,746 | 1/1960 | Gratacos | 195/96 X |
| 3,046,201 | 7/1962 | White et al. | 195/100 |
| 3,646,239 | 2/1972 | Hutson, Jr. et al. | 260/680 E |
| 3,794,582 | 2/1974 | Lackme et al. | 210/62 X |
| 3,844,893 | 10/1974 | Hitzman | 195/115 |
| 3,982,998 | 9/1976 | Hitzman et al. | 195/49 |
| 4,033,821 | 7/1977 | Urakami et al. | 195/82 X |

*Primary Examiner*—R. B. Penland

[57] ABSTRACT

Growth of yeasts requiring organic growth factors such as vitamins in an aerobic fermentation process is improved by dechlorination of residual chlorine from residual chlorine-containing make-up water.

14 Claims, No Drawings

TREATMENT OF MAKE-UP WATER FOR USE IN A FERMENTATION PROCESS FOR GROWTH OF YEAST CELLS REQUIRING GROWTH FACTORS

FIELD OF THE INVENTION

The invention relates to fermentation processes employing yeasts.

BACKGROUND OF THE INVENTION

Fermentation processes are widely used for a variety of purposes, chemical conversions, preparation of various beverages, and preparation of single cell proteins. For most industrial fermentations, tap water is used in preparing the make-up mineral media. Tap water, in most instances, contains residual chlorine, as required in most systems for control of disease-causing microorganisms. Certainly, the use of commonly available water sources, such as from municipal sources, is desirable in order to provide a minimum cost commercial operation.

BRIEF DESCRIPTION OF THE INVENTION

I have discovered that chlorine, even in the concentrations as are commonly present in most tap waters, has the unfortunate capability of inhibiting satisfactory growth rates of microbial cultures requiring growth factors such as biotin and thiamine for their satisfactory growth. This is particularly objectionable in single cell protein production, and most particularly with yeast cultures.

I have discovered that chemical or physical removal of residual chlorine from residual chlorine-containing make-up water for use in a fermentation process employing cultures requiring such growth factors distinctly improves the fermentation, permitting improved rates of growth. This is particularly important for improved yields in the production of single cell protein, and most particularly for yeasts since yeasts in particular have exhibited difficulty in growth employing mineral media prepared with residual-chlorine containing make-up water. Yeasts potentially are desirable in single cell protein production since the cell sizes of yeasts generally are larger than for bacteria, thus making handling and separation steps easier.

DETAILED DESCRIPTION OF THE INVENTION

I have discovered that the residual chlorine in water tends to render less effective or even ineffective growth factors, such as biotin, thiamine, or both, needed in culturing of most bacteria and yeasts. In accordance with my invention, in an aerobic fermentation process wherein yeast or bacteria microorganisms are cultured, employing a suitable substrate and an aqueous mineral medium prepared from water containing residual chlorine, the microorganisms further requiring at least one organic growth factor, such as biotin or thiamine, the residual chlorine is removed either by deactivation or by autoclaving before the required organic growth factors are added to the medium. As used herein, the term "residual chlorine" refers to chlorine as measured by the well known o-tolidine method of residual chlorine determination, using a Hellige pocket comparator.

The chlorine in the water tends to render less effective, or ineffective, possibly by change or modification which is presently uncharacterized, but nevertheless does adversely affect these growth factors necessary for the growth of the microorganism.

The residual chlorine can be removed from the chlorine-containing water either before or after admixing in the water the mineral nutrients necessary for growth of the microorganisms. As used herein, when I refer to a "residual chlorine-containing water" it means that water either as received, in the plant, or containing added mineral nutrients for makeup to the fermentation means.

The water containing residual chlorine can be treated by any procedure suitable and convenient to substantially remove all residual chlorine contained in the make-up water, rendering the residual chlorine content of the make-up water substantially zero. The residual chlorine can be removed by physical or chemical treatment, or both. Removal of the residual chlorine from the water can be accomplished by autoclaving or aeration of the tap water prior to addition of the minerals, or after, so long as the treatment is prior to the time the organic growth factors such as biotin or thiamine or both are added to the water. Autoclaving and aeration are each effective, and particularly effective in combination. Chemical treatment to inactivate the chlorine in the water also is effective, with or without autoclaving.

In a presently preferred procedure, the residual chlorine in the water is removed chemically by treatment of the water with a reducing agent whereby the residual chlorine is converted to an innocuous form, such as to chloride. Such a reducing agent should be of a type and character effective to remove the residual chlorine of the water, and itself not be toxic under the fermentation procedures to be employed.

Suitable reducing agents include alkali metal thiosulfates, i.e., lithium thiosulfate, sodium thiosulfate, potassium thiosulfate, rubidium thiosulfate, and cesium thiosulfate; alkali metal sulfites, i.e., lithium sulfite, sodium sulfite, potassium sulfite, rubidium sulfite, and cesium sulfite; alkali metal bisulfites, i.e., lithium bisulfite, sodium bisulfite, potassium bisulfite, rubidium bisulfite, and cesium bisulfite; alkali metal metabisulfites, i.e., lithium metabisulfite, sodium metabisulfite, potassium metabisulfite, rubidium metabisulfite, and cesium metabisulfite; alkali metal sulfides, i.e., lithium sulfide, sodium sulfide, potassium sulfide, rubidium sulfide, and cesium sulfide; alkali metal bisulfides, i.e., lithium bisulfide, sodium bisulfide, potassium bisulfide, rubidium bisulfide, and cesium bisulfide; sulfur dioxide; hydrogen sulfide; readily reduced organic compounds, e.g., thioglycolic acid, glutathione, cysteine, and dithiothreitol; and the like; and mixtures thereof. The reducing agent presently preferred is sodium thiosulfate because it is cheap, readily available, introduces no unusual elements, and has been found to function particularly well.

The amount of the reducing agent should be that which is sufficient to effectively remove the chlorine contained in the water. The amount of the reducing agent added is that amount which, based on the oxidation-reduction reaction involved, is at least in accordance with stoichiometric requirements. In general, larger amounts of reducing agent can be employed, such as amounts of up to 100 percent or more in excess of the stoichiometric amount, since generally there are only a few parts per million, frequently even less than 1 part per million, of chlorine contained in residual chlorine-containing water, so that the amount of reducing agent usually will be quite small, though exceedingly important in the case of use with microorganisms which require organic growth factors such as biotin or thiamine for their proper growth.

When using an alkali metal thiosulfate, such as sodium thiosulfate, the stoichiometric requirement is 2 moles of the alkali metal thiosulfate per mole of residual chlorine.

Contacting conditions for removal, inactivation, or reduction of the residual chlorine by chemical means are those conditions of time and temperature suitable for the effects desired using the particular chemical agent involved. Generally, the time will be quite short, such as about 30 seconds, to perhaps 4 hours, presently preferred about 5 minutes to 40 minutes. The temperature employed for residual chlorine removal by a reducing agent can be any temperature at which the residual chlorine-containing water is in the liquid phase, temperatures such as in the range of about 10° C. to 30° C. being convenient.

An alternative mode for removal of the residual chlorine from a residual chlorine-containing water is by heating, such as by autoclaving. The residual chlorine-containing water can be heated to such as about 100° C. to 150° C., for a few minutes such as about 5 minutes to upwards of 2 hours or more, at any convenient pressure, such as within the range of about atmospheric pressure to about 54 psig or more. 54 psig is frequently used in autoclaving since this is the pressure exerted by saturated steam at 150° C., a steam pressure often readily available.

In another mode, residual chlorine can be removed from the residual chlorine-containing make-up water by spraying the residual chlorine-containing make-up water into air or an inert gas such as nitrogen, or by passing the air or inert gas such as nitrogen through the residual chlorine-containing water. The use of air rather than inert gas presently is preferred in this mode in view of the obviously more favorable economics. By this method, the residual chlorine-containing water is treated in the liquid state by maintaining it in a thorough intimate contact with the air or inert gas for a period of time sufficient to remove substantially all of the residual chlorine, such as over a time of about 0.5 hr. to 3 hrs., employing a suitable temperature such as ambient temperature such as about 10° C. to 30° C., generally at substantially atmospheric pressure for convenience.

A combination of autoclaving followed by aeration presently is considered quite effective, though obviously less economically attractive than chemical removal.

In a further mode, the residual chlorine can be removed from the residual chlorine-containing water by contacting the residual chlorine-containing water with an effective absorbent such as activated carbon in an amount and for a time sufficient to remove substantially all of the residual chlorine, such treatment normally being at ambient temperature such as 10° C. to 30° C. at substantially atmospheric pressure.

In each of the methods described for residual chlorine removal, it is preferable, though not necessary, that the residual chlorine be removed from the residual chlorine-containing water prior to addition of minerals desired for growth of the microorganisms in the fermentation process.

MICROORGANISMS

Although the microorganisms for use in the fermentation process can be species of either yeasts or bacteria which require an organic growth factor such as biotin and/or thiamine, the invention is particularly applicable to the use of yeasts in view of the more general need for organic growth factors such as biotin and/or thiamine in fermentations conducted with yeasts.

Yeasts used in the process of this invention typically include species from the genera Candida, Hansenula, Torulopsis, Saccharomyces, Pichia, Debaryomyces and Brettanomyces. The preferred genera include Candida, Hansenula, Torulopsis, Pichia, and Saccharomyces. Examples of suitable species include:

| | |
|---|---|
| Brettanomyces petrophilium | Hansenula philodendra |
| Candida boidinii | Pichia farinosa |
| Candida lipolytica | Pichia polymorpha |
| Candida mycoderma | Pichia membranefaciens |
| Candida utilis | Pichia pinus |
| Candida stellatoidea | Pichia pastoris |
| Candida robusta | Pichia trehalophila |
| Candida claussenii | Saccharomyces cerevisiae |
| Candida rugosa | Saccharomyces fragilis |
| Candida tropicalis | Saccharomyces rosei |
| Candida maltosa | Saccharomyces acidifaciens |
| Debaryomyces hansenii | Saccharomyces elegans |
| Hansenula minuta | Saccharomyces rouxii |
| Hansenula saturnus | Saccharomyces lactis |
| Hansenula californica | Torulopsis sonorensis |
| Hansenula mrakii | Torulopsis candida |
| Hansenula silvicola | Torulopsis bolmii |
| Hansenula polymorpha | Torulopsis versatilis |
| Hansenula wickerhamii | Torulopsis glabrata |
| Hansenula capsulata | Torulopsis molishiana |
| Hansenula glucozyma | Torulopsis nemodendra |
| Hansenula henricii | Torulopsis nitratophila |
| Hansenula nonfermentans | Torulopsis pinus |

If desired, mixtures of two or more species of yeasts can be employed.

Exemplary bacteria include species from the genera Bacillus, Mycobacterium, Actinomyces, Nocardia, Pseudomonas, Methanomonas, Protaminobacter, Methylococcus, Arthrobacter, Methylomonas, Brevibacterium, Acetobacter, Micrococcus, Rhodopseudomonas, Corynebacterium, Microbacterium, Achromobacter, Methylobacter, Methylosinum, Methylocystis, and Acinetobacter. If desired, mixtures of two or more species of bacteria can be used.

The particular yeast or bacterium employed depends in part on the carbon-containing substrate to be used since it is well known that different yeasts or bacteria often require different substrates for growth.

The carbon and energy source material or substrate for the fermantation process in accordance with my invention can be any suitable carbon and energy source, such as hydrocarbons, oxygenated hydrocarbons, including various carbohydrates, and the like, suitable as substrates for yeasts or bacteria.

As will be recognized by those skilled in the art, the carbon-containing substrate selected should be one or more on which the yeast or bacteria to be employed will grow suitably. As is well known, various bacteria or yeasts have preferences for the type of substrate employed in general.

My discovery of a problem in using chlorine-containing make-up water, and my solution thereto, applies to any fermentation process using a microorganism requiring an organic growth factor for adequate growth rates to effect the conversion or production desired.

Most important at the present time of world protein shortages are processes of fermentation for the production of single cell protein.

The presently preferred substrates for aqueous fermentation conditions for single cell protein production are the carbon-oxygen-hydrogen-containing compounds of sufficient significant water-solubility as to permit their use as a carbon energy substrate in an aqueous fermentation process. The term "oxygenated hydrocarbon" is intended to be a generic term descriptive of the compounds employable, and not necessarily a limiting term referring to the source of the substrate. As such, the oxygenated hydrocarbons include the carbohydrates, as well as the alcohols, ketones, esters, acids and aldehydes, which are significantly water-soluble in character. For reasons of solubility, the oxygenated hydrocarbons, though broadly of some water-soluble character, generally are of 1 to 20 carbon atoms per molecule, and usually are those of substantially more water solubility of up to such as about 10 carbon atoms per molecule or water-soluble carbohydrates, depending on the particular material involved.

Among the exemplary carbohydrates are glucose, fructose, galactose, lactose, sucrose, starch, dextrin, and the like, including mixtures.

Of other types of oxygenated hydrocarbons, exemplary species include methanol, ethanol, ethylene glycol, propylene glycol, 1-propanol, 2-propanol; glycerol, 1-butanol, 2-butanol, 3-methyl-1-butanol, 1-pentanol, 2-hexanol, 1,7-heptanediol, 1-octanol, 2-decanol, 1-hexadecanol, 1-eicosanol, acetone, 2-butanone, 4-methyl-2-pentanone, 2-decanone, 3-pentadecanone, 2-eicosanone, formaldehyde, acetaldehyde, propionaldehyde, butyraldehyde, hexanal, 7-methyloctanal, tetradecanal, eicosanal, formic acid, acetic acid, propionic acid, butyric acid, glutaric acid, 5-methylhexanoic acid, azelaic acid, dodecanoic acid, eicosanoic acid, methyl formate, methyl acetate, ethyl acetate, propyl butyrate, isopropyl hexanoate, hexyl 5-methyloctanoate, octyl dodecanoate, and the like, including mixtures thereof.

Of the hydrocarbons, the normal paraffins can be employed, such as those of 1 to 20 carbon atoms per molecule, including the exemplary methane, ethane, propane, butane, pentane, octane, decane, undecane, dodecane, tridecane, tetradecane, pentadecane, hexadecane, octadecane, eicosane, and the like, including mixtures.

Of course, mixtures of 1 or more materials from each of any of the above groups can be employed.

Of the carbon-containing substrates, presently and most preferred are the water-soluble alcohols and acids of 1 to 4 carbon atoms, and the water-soluble carbohydrates, the alcohols of 1 to 4 carbon atoms being more preferred because of ready availability and costs, and of these methanol and ethanol are preferred over the others, methanol being most preferred for availability and cost.

Petroleum gases can be oxidized, and the water-soluble materials employed. The oxidation of such as methane, ethane, and the like, provide suitable mixtures predominantly of the corresponding alcohol as well as various aldehydes, ketones, acids, and the like. Similarly, hydrocarbon fractions from various petroleum refinery sources produced within the modern refining and chemical processing plant complex, sometimes termed a petrocomplex, can be utilized for fermentation purposes.

FERMENTATION CONDITIONS

Culturing is accomplished in a growth medium comprising an aqueous mineral salts medium, organic growth factors, the carbon and energy source material, molecular oxygen, and, of course, a starting inoculum of one or more particular microorganism species to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation media.

The composition of the aqueous mineral medium can vary over a wide range, depending in part on the microorganism and substrate employed, as is known in the art. The mineral media should include, in addition to nitrogen, suitable amounts of phosphorus, magnesium, calcium, potassium, sulfur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

In addition to the minerals, organic growth factors are desirable for the propagation of the particular yeast or bacteria culture being grown. Many yeasts and bacteria appear to require the presence of one or both of the vitamins biotin and thiamine for their proper propagation. Thus, with a yeast such as *Hansenula polymorpha*, it is desirable to employ biotin in an amount of about 0.04 to 0.8 milligram per liter of aqueous mineral medium, and thiamine in an amount of about 4 to 80 milligrams per liter of aqueous mineral medium. Alternatively, all or part of the biotin and thiamine can be provided by use of yeast extract or the like.

The fermentation reaction is an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species in growing in a thriving fashion. In effect, by using an oxygenated hydrocarbon substrate, the oxygen requirement for growth of the microorganism is reduced. Nevertheless, molecular oxygen must be supplied for growth, since the assimilation of the substrate and corresponding growth of the microorganisms, is, in part, a combustion process.

Although the aeration rate can vary over a considerable range, aeration generally is conducted at a rate which is in the range of about 0.5 to 8, preferably about 0.7 to 6, volumes (at the pressure employed and at 25° C.) of oxygen-containing gas per liquid volume in the fermentor per minute. This amount is based on air of normal oxygen content being supplied to the reactor, and in terms of pure oxygen the respective ranges would be about 0.1 to 1.7, or preferably about 0.1 to 1.3, volumes (at the pressure employed and at 25° C.) of oxygen per liquid volume in the fermentor per minute.

The pressure employed for the microbial conversion process can range widely. Pressures generally are within the range of about 0 to 150 psig, presently preferably about 0 to 60 psig, more preferably at least slightly over atmospheric pressure, as a balance of equipment and operating cost versus oxygen solubility achieved. Greater than atmospheric pressures are advantageous in that such pressures do tend to increase a dissolved oxygen concentration in the aqueous ferment, which in turn can help increase cellular growth rates. At the same time this is balanced by the fact that high atmospheric pressures do increase equipment and operating costs.

The fermentation temperature can vary somewhat, but for yeasts as well as for bacteria generally will be within the range of about 25° C. to 65° C., generally preferably in the range of about 28° C. to 55° C., depending on the microorganism strain chosen.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 3 to 8. With yeasts, the pH normally is within the range of about 3 to 7; with bacteria, the pH normally is within the range of about 5 to 8. pH range preferences for certain microorganisms are dependent on the media employed to some extent, as well as the particular microorganism, and thus change somewhat with change in media as can be readily determined by those skilled in the art.

While the average retention time of the fermentation admixture in the fermentor can vary considerably, depending in part on the fermentation temperature and culture employed, generally it will be within the range of about 2 to 30 hours, preferably presently about 4 to 14 hours.

High concentrations of some of the described carbon and energy substrates, such as methanol, or formaldehyde, or the like, may be inhibitory to satisfactory microbial growth or even toxic to some microorganisms employed in fermentations. Relatively high concentrations of such substrates thus should be avoided, so that it is generally desirable to maintain the substrate concentration in the fermentation admixture at a maximum tolerable level. With some of the lower alcohols, aldehydes, and the like, this level generally is in the range of about 0.001 to 5 volume percent, preferably about 0.01 to 0.05 volume percent, so as to neither starve nor inhibit the growth rates of the microorganisms chosen.

When the carbon and energy source material contains an aldehyde in amounts potentially deleterious to the microorganism, the deleterious aldehyde effects can be alleviated by first treating the substrate with a suitable amount of a nitrogen-containing compound, preferably ammonia, ammonium hydroxide, or other active ammonium compound, in a ratio of about 0.01 to 10 mol equivalents per mol of aldehyde. Such a treated substrate then is not only the carbon and energy source, but also contains at least a portion of the necessary assimilable nitrogen.

Preferably, the fermentation is conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily washed off. It may be a problem, however, in the case of non-water-soluble substrates such as the higher hydrocarbons, and require added product-treatment steps such as removal of residual hydrocarbon by suitable washing steps.

Although the fermentation can be conducted as a batch or semi-continuous operation, continuous operation is much to be preferred for ease of control, production of uniform quantities of uniform products, and most economical uses of all equipment. In a continuous process, the carbon and energy source material as substrate, aqueous mineral medium, assimilable nitrogen source, and molecular oxygen-containing gases, are added continuously to the ferment in the fermentor, and the ferment continuously withdrawn for processing, separation of cells, and the like.

Although the weight ratio of added carbon-containing substrate:added aqueous mineral medium can vary over a wide range, depending in part on the nature of the carbon-containing substrate, generally it will be in the range of about 0.4:9.6 to 5:5, presently preferably in the range of about 0.6:9.4 to 4.5:5.5.

If desired, part or all of the carbon and energy source material and/or part of the assimilable nitrogen source such as ammonia can be added to the aqueous mineral medium prior to feeding the aqueous mineral medium to the fermentor.

Each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermentor, cell density measurable by light transmittancy, or the like. The feed rates of the various materials can be varied so as to obtain as rapid a cell growth rate as possible, consistent with efficient utilization of the carbon and energy source, to obtain as high a yield of microorganism cells relative to substrate charge as possible.

In either a batch, or the preferred continuous operation, all equipment, reactor, or fermentation means, vessel or container, piping, attendant circulating or cooling devices, and the like, are initially sterilized, usually by employing steam such as at about 250° F. (121° C.) for at least about 15 minutes. The sterilized reactor then is inoculated with a culture of the selected microorganism in the presence of all the required nutrients, including oxygen, and the carbon-containing substrate.

The type of fermentor employed is not critical, though presently preferred is operation under substantially foam-filled conditions.

PRODUCT RECOVERY

The cells produced can be recovered from the fermentation admixture effluent by conventional means, such as by centrifugation or filtration. If desired, extracellular products can be recovered from the substantially cell-free remaining liquid by conventional means. The substantially cell-free effluent can be treated, for example, with acetone or a lower alcohol such as methanol or ethanol to precipitate any polymeric material produced extra-cellularly. The cell-free effluent also can be treated by solvent extraction and/or base extraction to recover, if desired, other extra-cellular products such as pigments, vitamins, or the like, produced during the culturing process. The cell-free effluent, with or without such intervening treatment, can be returned to the fermentor as a part of the aqueous makeup, or as a substantial or almost total part of the aqueous makeup, to avoid problems with the waste disposal insofar as possible.

The microbial cells usually are killed by heat or chemical means, and this can be done before or after the separation of the cells from the fermentor effluent. The cells are a valuable source of protein. For human consumption, the cells can be treated if necessary to reduce the nucleic acid, but for animal feed purposes, such treatment does not appear presently necessary.

EXAMPLES

The following are descriptive runs employing the process in accordance with my discovery. Particular amounts of materials, or particular types of feedstocks employed, particular species or strains of yeast, should be considered as illustrative and not as limitative of my invention.

In the following Examples, the fermentations were conducted at substantially atmospheric pressure in a 4-liter fermentor with a 2-liter working volume. The fermentor was set up for continuous operation, with pH control, temperature control, and dissolved oxygen read-out. Oxygen was supplied by enriching air with oxygen so as to keep the dissolved oxygen in the fermentation mixture at a level about 15 percent of that which would be dissolved in the fermentation mixture saturated with air at atmospheric pressure at the fermentation temperature employed. Agitation was provided by two impellers operating at about 1000 rpm. The pH was controlled at about 3.4–4.0 by the addition of aqueous ammonium hydroxide (3 parts concentrated ammonium hydroxide and 1 part deionized water by volume). The temperature was controlled at about 30° C. in the fermentation with the *Pichia pastoris* yeast culture and at about 40° C. in the fermentation with the *Hansenula polymorpha* yeast culture.

The aqueous mineral media used in the fermentations, except where otherwise stated, are herein designated as FM-12 and FM-16 aqueous mineral media. Each of these media contained methanol as the carbon-containing substrate for assimilation by the microorganisms.

The FM-12 aqueous mineral medium was prepared by mixing, for each liter of solution, 2 ml 85 percent $H_3PO_4$, 1 g KCl, 1.5 g $MgSO_4.7H_2O$, 0.2 g $CaCl_2.2H_2O$, 0.1 g NaCl, 5 ml trace mineral solution A, 1 ml of a biotin-thiamine hydrochloride growth factor solution, 100 ml methanol, about 2 drops of a commercial antifoam agent (Mazu DF-37C), and sufficient tap water of usual chlorine residual due to Bartlesville, Okla. city chlorination procedures, to make 1 liter of solution. Trace mineral solution A was prepared by mixing, for each liter of solution, 0.06 g $CuSO_4.5H_2O$, 0.08 g KI, 0.30 g $MnSO_4.H_2O$, 0.20 g $Na_2MoO_4.2H_2O$, 0.02 g $H_3BO_3$, 2.00 g $ZnSO_4.7H_2O$, 4.80 g $FeCl_3.6H_2O$, 3 ml $H_2SO_4$, and sufficient deionized water (chlorine-free) to make 1 liter of solution. The biotin-thiamine hydrochloride solution was prepared by mixing, for each 100 ml of solution, 4 mg biotin, 400 mg thiamine hydrochloride, and sufficient deionized water (chlorine-water) to make 100 ml of solution.

The FM-16 aqueous mineral medium was prepared by mixing, for each liter of solution, 2.5 ml 85 percent $H_3PO_4$, 0.5 g KOH, 1.5 g KCl, 1.5 g $MgSO_4.7H_2O$, 0.2 g $CaCl_2.2H_2O$, 5 ml trace mineral solution B, 2 ml of the biotin-thiamine hydrochloride solution, 100 ml methanol, about 2 drops of antifoam agent, and sufficient tap water of usual chlorine residual due to city chlorination procedures, to make 1 liter of solution. The biotin-thiamine hydrochloride solution was the same as that described for use in preparing the FM-12 aqueous mineral medium. Trace mineral solution B was prepared by mixing, for each liter of solution, 6.5 g $FeCl_3.6H_2O$, 1.8 g $ZnSO_4.7H_2O$, 0.6 g $CuSO_4.5H_2O$, 0.5 g $MnSO_4.H_2O$, 2 ml $H_2SO_4$, and sufficient deionized water (chlorine-free) to make 1 liter of solution.

The chlorine content, where shown, is the residual chlorine concentration as determined by the o-tolidine method, using a Hellige pocket comparator.

EXAMPLE I

A run was conducted in which FM-16 aqueous mineral medium and the yeast *Pichia pastoris* NRRL Y-1603 were employed. As the feed rates of the aqueous mineral medium were increased to result in an average retention time in the fermentor of about 8 hours, methanol began to build up in the ferment, and over a weekend the growth of the microorganisms was so inhibited that the culture washed out even at an average retention time extended to about 13.5 hours. This washing out of the culture did not occur in earlier runs in which the only water used in preparing the mineral media was deionized water, other operating factors being the same. "Washing out" means that the growth rate is slower than the retention time, so that the cells are being washed out of the fermentor faster than they are being produced. The term is well recognized in the art. These runs demonstrate the undesirable growth-inhibiting effects of tap water containing residual chlorine.

EXAMPLE II

In this run the FM-16 medium was prepared as described above except omitting the biotin-thiamine hydrochloride solution and the antifoam agent, and autoclaved at 121° C. for 30 minutes to remove residual chlorine. The biotin-thiamine growth factor solution and the anti-foam then were added to the autoclaved medium, after cooling, to complete the FM-16 medium. The yeast culture employed was the same as that employed in the runs of Example I. The average retention time in the fermentor was maintained at about 8 hours. The run progressed normally without signs of inhibition.

Thereupon, sufficient chlorine in the form of dilute sodium hypochlorite (household bleach) was added until a residual chlorine of 7 ppm was obtained in the aqueous mineral medium prior to its introduction into the fermentor, whereupon the methanol content in the aqueous ferment in the fermentor rose from 0.005 volume percent to a final concentration of 0.89 volume percent over a period of 16 hours, indicating that inhibition of growth of the microorganisms was occurring. The level of residual chlorine in the mineral medium being fed to the fermentor at this time had decreased to 0.5 ppm. Yet growth inhibition continued. Clearly, chlorine inhibited growth of the microorganisms.

EXAMPLE III

A run was conducted in which FM-12 aqueous mineral medium (prepared with chlorine-containing tap water) and the yeast *Hansenula polymorpha* NRRL Y-11,170 were employed. To determine if residual chlorine in the make-up mineral medium affected the growth of this yeast culture as it did the *Pichia pastoris* culture used in the Runs of Examples I and II, the FM-12 medium was fed continuously to the fermentor. Even at a high average retention time in the fermentor of 11.3 hours, the methanol concentration built up, clearly indicating inhibition of growth of the microorganisms on the medium prepared from tap water without a dechlorination step.

A medium prepared in the same manner as the FM-12 medium except without methanol and without the biotin-thiamine hydrochloride growth factor solution was autoclaved at 121° C. for about 30 minutes and then aerated until substantially all of the residual chlorine was removed prior to addition of the methanol and biotin-thiamine hydrochloride solution. The resulting medium then was fed to the fermentor for 24 hours, replacing the starting medium, the feed rate being increased to reduce the average retention time in the fermentor to 8.51 hours, yet without encountering a microorganism growth problem. Thus, it was clear that autoclaving and aeration had removed the microorganism growth inhibition component, i.e., chlorine, present in the tap water, prior to contact with the growth factors.

Then, a medium was prepared in the same way as the FM-12 medium except that the tap water employed in the preparation of the medium was autoclaved at 121° C. for about 30 minutes to remove residual chlorine, prior to use in the preparation of the medium. This medium, prepared from dechlorinated make-up water, was fed to the fermentor for about 64 hours during which time the average retention time in the fermentor was further reduced to 6.77 hours without noting any indication of microorganism inhibition such as methanol build-up. The yield of cells in this part of the Run was not quite as good as expected, however, and the culture was "off" color, i.e., slightly tan. Thus, there may have been some slight growth inhibiting effect, possibly due to incomplete chlorine removal.

For the next day a mineral medium comparable to the FM-12 mineral medium, except prepared from deionized water instead of tap water, was fed to the fermentor. Then the mineral medium feed was switched to a mineral medium comparable to the FM-12 mineral medium except that the tap water employed in its preparation was first aerated (12 liters water at about 20° C. aerated with 5 liters of air per minute for 1 hour) to remove substantially all of the residual chlorine. This aqueous mineral medium was fed to the fermentor for 27 hours with an average retention time in the fermentor of 7.1 hours without noting any microorganism growth inhibition.

Thus, the above Runs in this Example demonstrate that either aeration or autoclaving or a combination of the two removed or substantially reduced the inhibitory character of residual chlorine in the tap water on the growth of the microorganisms.

EXAMPLE IV

A Run was conducted using the *Hansenula polymorpha* as described in Example III, and using an aqueous mineral medium comparable to FM-16 aqueous mineral medium except that the residual chlorine in the tap water used in its preparation was neutralized with sodium thiosulfate prior to addition of the other components. The residual chlorine content of the tap water was first measured, and an equivalent quantity of sodium thiosulfate was added to neutralize the chlorine. For the next 7 days this aqueous mineral medium was run through the fermentor at increasing rates. Even near the maximum growth rate of the culture (5–5.5 hours average retention time in the fermentor) no problems resulted from use of the mineral medium prepared from the thiosulfate-treated water. Clearly, dechlorination of the residual chlorine in tap water with sodium thiosulfate was successful and, in view of its ease of operation, is the preferred method of avoiding the harmful effects of chlorine.

EXAMPLE V

In these Runs, the yeast employed was the *Hansenula polymorpha* culture employed in Example III, and the retention time of the aqueous mineral medium in the fermentor was 6.6–7.6 hours. In the first runs, the aqueous mineral medium fed to the fermentor was the same as FM-16 aqueous mineral medium except that the tap water used in its preparation was first treated with chlorine to increase the concentration of residual chlorine in the water to 1.0 ppm and 0.5 ppm, respectively. In each instance, employment of the aqueous mineral medium in a fermentation demonstrated that the presence of residual chlorine inhibited growth of the microorganisms. When the mineral media were prepared from the tap water to which additional chlorine had been added, as above, except that the aqueous mineral media were first autoclaved at 121° C. for 40 minutes prior to addition of the biotin and thiamine hydrochloride and the antifoam agent, substantially all residual chlorine was thereby removed and growth inhibition of the microorganisms did not occur in the fermentations which followed.

EXAMPLE VI

It appeared unlikely that chlorine at 0.5–1 ppm could actually kill the yeast and cause the growth inhibition which had been observed. It seemed more likely that chlorine was reacting with the methanol or with the organic growth factors biotin and thiamine to produce some growth-inhibitory compound or to inactivate the organic growth factors. To test this hypothesis, an aqueous mineral medium was prepared as above, using tap water which had been treated with chlorine to increase the chlorine concentration to 0.5 ppm, except that the methanol normally incorporated into the aqueous mineral medium was fed to the fermentor as a separate stream to avoid any reaction of chlorine with methanol which might occur while the solution was waiting to be fed to the fermentor. After the fermentation had been conducted for about 1 day, using the *Hansenula polymorpha* culture employed in Example III, it was observed that the concentration of methanol in the fermentor was rising, indicating inhibition of growth of the microorganisms. Thus, the growth inhibitiion problem was not caused by reaction of chlorine with the methanol in an aqueous mineral medium to be fed to the fermentor; instead, growth inhibition was caused by reaction of chlorine with the organic growth factors biotin and thiamine, thereby inactivating the growth factors or converting them to growth-inhibitory derivatives.

The disclosure, including data, has illustrated the value and effectiveness of my invention. The examples, the knowledge and background of the field of the invention and of general principles of the microbiological sciences have formed the bases from which the broad descriptions of the invention including the ranges of conditions have been developed, and have formed the bases for my claims here appended.

I claim:

1. In a process for aqueous biological fermentation employing at least one yeast or bacterial culture wherein said microorganism requires at least one organic growth factor for effective growth under aqueous aerobic fermentation conditions employing at least one organic growth factor, make-up water containing residual chlorine and a suitable carbon substrate, assimilable nitrogen source, molecular oxygen, and nutrient minerals, effective for growth of said at least one yeast or bacterial culture, said residual chlorine being present in amounts rendering said at least one growth factor less effective for growth of the microorganism, the step which comprises substantially removing said residual chlorine from said residual chlorine-containing make-up water to produce a residual chlorine content in said water of substantially zero prior to contact with said organic growth factors, said residual chlorine being removed by one treatment selected from the group consisting of using a reducing agent, aeration and a combination of heating and aeration, said treatment effective to render said residual chlorine content substantially zero.

2. The process according to claim 1 wherein said microorganism is a yeast selected from the genera Candida, Hansenula, Torulopsis, Saccharomyces, Pichia, Debaryomyces, and Brettanomyces.

3. The process according to claim 2 wherein said microorganism is selected from

| | |
|---|---|
| Brettanomyces petrophilium | Hansenula philodendra |
| Candida boidinii | Pichia farinosa |
| Candida lipolytica | Pichia polymorpha |
| Candida mycoderma | Pichia membranefaciens |
| Candida utilis | Pichia pinus |
| Candida stellatoidea | Pichia pastoris |
| Candida robusta | Pichia trehalophila |
| Candida claussenii | Saccharomyces cerevisiae |
| Candida rugosa | Saccharomyces fragilis |
| Candida tropicalis | Saccharomyces rosei |
| Candida maltosa | Saccharomyces acidifaciens |
| Debaryomyces hansenii | Saccharomyces elegans |
| Hansenula minuta | Saccharomyces rouxii |
| Hansenula saturnus | Saccharomyces lactis |
| Hansenula californica | Torulopsis sonorensis |
| Hansenula mrakii | Torulopsis candida |
| Hansenula silvicola | Torulopsis bolmii |
| Hansenula polymorpha | Torulopsis versatilis |
| Hansenula wickerhamii | Torulopsis glabrata |
| Hansenula capsulata | Torulopsis molishiana |
| Hansenula glucozyma | Torulopsis nemodendra |
| Hansenula henricii | Torulopsis nitratophila |
| Hansenula nonfermentans | Torulopsis pinus. |

4. The process according to claim 3 wherein said microorganism is *Pichia pastoris* NRRL Y-1603.

5. The process according to claim 3 wherein said microorganism is *Hansenula polymorpha* NRRL Y-11,170.

6. The process according to claim 1 wherein said microorganism is a bacterium and is selected from the genera Bacillus, Mycobacterium, Actinomyces, Nocardia, Pseudomonas, Methanomonas, Protaminobacter, Methylococcus, Arthrobacter, Methylomonas, Brevibacterium, Acetobacter, Micrococcus, Rhodopseudomonas, Corynebacterium, Microbacterium, Achromobacter, Methylobacter, Methylosinus, Methylocystis, and Acinetobacter.

7. The process according to claim 6 wherein said residual chlorine is removed by chemical treatment using an effective amount of a reducing agent.

8. The process according to claim 7 wherein said reducing agent is selected from lithium thiosulfate, sodium thiosulfate, potassium thiosulfate, rubidium thiosulfate, cesium thiosulfate, lithium sulfite, sodium sulfite, potassium sulfite, rubidium sulfite, cesium sulfite, lithium bisulfite, sodium bisulfite, potassium bisulfite, rubidium bisulfite, cesium bisulfite, lithium metabisulfite, sodium metabisulfite, potassium metabisulfite, rubidium metabisulfite, cesium metabisulfite, lithium sulfide, sodium sulfide, potassium sulfide, rubidium sulfide, cesium sulfide, lithium bisulfide, sodium bisulfide, potassium bisulfide, rubidium bisulfide, cesium bisulfide, sulfur dioxide, hydrogen sulfide, thioglycolic acid, glutathione, cysteine, dithiothreitol, and mixtures.

9. The process according to claim 6 wherein said residual chlorine is removed by intimately contacting the water with amounts of a residual chlorine-removing gas selected from air and nitrogen effective to render said residual chlorine content substantially zero.

10. The process according to claim 6 wherein said residual chlorine is inactivated by a combination of heating and aeration effective to inactivate residual chlorine.

11. The process according to claim 1 wherein said organic growth factor comprises at least one of biotin and thiamine, said process produces a single cell protein, employs a yeast, and an oxygenated hydrocarbon substrate.

12. The process according to claim 1 employing methanol.

13. The process according to claim 12 employing a *Pichia pastoris* or *Hansenula polymorpha*.

14. The process according to claim 13 employing sodium thiosulfate in treating said residual chlorine-containing water to remove said residual chlorine.

* * * * *